United States Patent [19]

McMillan et al.

[11] Patent Number: 4,466,977

[45] Date of Patent: * Aug. 21, 1984

[54] N-[2-AMINO(OXY- OR THIA-GROUP-SUBSTITUTED-CYCLOALIPHATIC)]BENZENEACETAMIDES AND -BENZAMIDE ANALGESICS

[75] Inventors: Moses W. McMillan, Portage; Jacob Szmuszkovicz, Kalamazoo, both of Mich.

[73] Assignee: The Upjohn Company, Kalamazoo, Mich.

[*] Notice: The portion of the term of this patent subsequent to Nov. 23, 1999 has been disclaimed.

[21] Appl. No.: 439,103

[22] Filed: Nov. 4, 1982

Related U.S. Application Data

[63] Continuation-in-part of Ser. No. 252,535, Apr. 9, 1981, Pat. No. 4,360,531.

[51] Int. Cl.$^3$ .................... C07D 207/08; A61K 31/40
[52] U.S. Cl. ....................................... 424/274; 548/578; 546/234; 260/239 A; 260/349; 424/244; 424/267; 424/301; 424/311; 424/324; 424/309; 560/17; 560/251; 564/163; 564/164; 564/165; 564/166; 564/182; 564/183

[58] Field of Search ............... 424/274, 244, 267, 309, 424/311, 324, 301; 548/578; 546/234; 260/239 A, 349; 560/17, 251; 564/163, 164, 165, 166, 182, 183

[56] References Cited

U.S. PATENT DOCUMENTS

| | | | |
|---|---|---|---|
| 3,510,492 | 5/1970 | Szmuszkovicz | 546/232 |
| 4,065,573 | 12/1977 | Lednicer | 424/278 |
| 4,098,904 | 7/1978 | Szmuszkovicz | 424/324 |
| 4,145,435 | 3/1979 | Szmuszkovicz | 424/274 |
| 4,212,878 | 7/1980 | Lednicer | 424/274 |
| 4,360,531 | 11/1982 | McMillan et al. | 424/274 |

*Primary Examiner*—Jane T. Fan
*Attorney, Agent, or Firm*—John T. Reynolds

[57] ABSTRACT

Cis- and trans-N-[2-amino(oxy- or thia group-substituted-cycloaliphatic)]benzeneacetamide and -benzamide compounds, e.g., 3,4-dichloro-N-[4,4-dimethoxy-2-(1-pyrrolidinyl)cyclohexyl]-N-methylbenzeneacetamide, and salts thereof, are provided. These compounds have analgesic properties. Processes for their preparation are disclosed. Pharmaceutical compositions and methods of use are also provided.

8 Claims, No Drawings

N-[2-AMINO(OXY- OR THIA-GROUP-SUBSTITUTED-CYCLOALIPHATIC)]BENZENEACETAMIDES AND -BENZAMIDE ANALGESICS

CROSS REFERENCE

This is a continuation-in-part of application Ser. No. 06/252,535, filed Apr. 9, 1981, now U.S. Pat. No. 4,360,531, issued Nov. 23, 1982.

INTRODUCTION

This invention relates to N-[2-amino(oxy- or thia-group-substituted-cycloaliphatic)]benzeneacetamide and -benzamide compounds. More particularly, this invention provides some new N-[2-amino-(oxy- or thia-group-substituted-cycloaliphatic)]benzeneacetamide and -benzamide compounds which have useful analgesic activity and low abuse liability. Processes for their preparation are disclosed. Pharmaceutical compositions and methods of use are also provided.

BACKGROUND OF THE INVENTION

Szmuszkovicz U.S. Pat. No. 4,145,435 discloses some cis- and trans-N-(2-aminocycloaliphatic)-2-arylacetamide derivative compounds, e.g., N-[2-(N',N'-dimethylamino)cyclohexyl]-N-methyl-2-(4-bromophenyl)-acetamide and trans-N-methyl-N-[2-(1-pyrrolidinyl)cyclohexyl]-2-(3,4-dichlorophenyl)acetamide, which have potent analgesic activity; the preferred compounds thereof have, in addition, only low to moderate apparent physical dependence liability compared to morphine and methadone.

Also, Szmuszkovicz U.S. Pat. No. 4,098,904 discloses some cis- and trans-N-(2-aminocycloaliphatic)benzamide compounds, e.g., N-methyl-N-(2-aminocycloaliphatic)benzamide compounds, e.g., N-methyl-N-[2-(1-pyrrolidinyl)cyclohexyl]-3,4-dichlorobenzamide, which have potent analgesic activity, making them useful for relieving pain in warm-blooded animals.

Lednicer U.S. Pat. No. 4,212,878 discloses some N-[(1-amino-4-(mono- or di-oxygen-group-substituted)cyclohexyl)methyl]benzeneacetamide derivatives, e.g., 2-(3,4-dichlorophenyl)-N-[[8-(1-pyrrolidinyl)-1,4-dioxaspiro[4.5]dec-8-yl]methyl]acetamide, which also have analgesic drug properties with lower physical dependence liability characteristics than morphine or methadone. That Lednicer patent also refers to what is now Lednicer U.S. Pat. No. 4,065,573 which discloses some 4-amino-4-phenylcyclo hexanone keta compounds, e.g., 4-(m-hydroxyphenyl)-4-(dimethylamino)cyclohexanone ethylene ketal and 4-(m-hydroxyphenyl)-4-(n-butylmethylamino)cyclohexanone ethylene ketal, which are useful for relieving pain in animals, some of which compounds exhibit narcotic antagonist activity.

More recently, in the above identified cross-referenced application, we described and claimed some new 2-aminocycloaliphatic-benzeneacetamide and -benzamide compounds bearing oxy- or thia-group substituents on a cycloaliphatic ring carbon not adjacent to the nitrogen bearing carbons of that cycloaliphatic ring, e.g., trans-3,4-dichloro-N-methyl-N-[7-(1-pyrrolidinyl)-1,4-dioxaspiro[4.5]dec-8-yl]-benzeneacetamide, and salts thereof, which were found to have useful ranges of analgesic properties while also having low apparent physical dependence liability properties. Those compounds were described by the general formula (I):

wherein p and n are each full number integers of from 1 to 3, so that the resulting cycloaliphatic ring has five to seven carbon atoms; the wavy line bond (~) between the nitrogen in the 2-position and the cycloaliphatic ring carbon indicates the bond can be either cis- or trans- with respect to each substituent of the cycloaliphatic ring;

q is 0 or 1;

X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxyacylamino [(-NHC(O)R$_6$)];

R is hydrogen or $C_1$ to $C_3$-alkyl;

$R_1$ and $R_2$, taken separately, are hydrogen, $C_1$ to $C_3$-alkyl, allyl, or $R_1$ and $R_2$, taken together with the nitrogen to which they are bonded, complete a ring selected from the group consisting of azetidinyl, pyrrolidinyl and piperidinyl;

$R_3$, taken separately, is hydrogen, hydroxy, —OR$_5$ or OC(=O)R$_6$;

$R_4$, taken separately, is hydrogen;

$R_3$ and $R_4$, taken together, are selected from the group consisting of
—ECH$_2$CH$_2$E—,
=E,
=N~OH, and
=N~OC(O)CH$_3$, wherein each E is bivalent sulfur or oxygen, and $R_3$ and $R_4$ cannot both by hydrogen at the same time;

$R_5$ is $C_1$ to $C_3$-alkyl;

$R_6$ is H, or $C_1$ to $C_2$-alkyl; and the acid addition salts thereof, particularly pharmaceutically acceptable salts thereof.

The above general Formula I compounds, particularly at the $R_3$ and $R_4$ substituent definitions, do not include the compounds of this invention.

OBJECTS OF THE INVENTION

It is an object of this invention to provide some new N-[2-amino-(oxy- or thia-group-substituted-cycloaliphatic)]benzeneacetamide and -benzamide compounds which are useful analgesic compounds.

Another object of the invention is to provide pharmaceutical compositions, useful in pharmaceutically effective dosage unit form for alleviating pain in mammals comprising a compound of Formula II in combination with a pharmaceutically acceptable carrier.

It is also an object of this invention to provide a method of alleviating pain in mammals with the above compounds and compositions.

Other objects, aspects, and advantages of the invention will become apparent from reading the remaining specification and the claims which follow.

SUMMARY OF THE INVENTION

Briefly, this invention provides some new 2-aminocycloaliphaticbenzeneacetamide and -benzamide compounds bearing certain oxy- or thia-group substituents on a cycloaliphatic ring carbon atom not adjacent to the nitrogen bearing carbons of that cycloaliphatic ring, e.g., 3,4-dichloro-N-[4,4-dimethoxy-2-(1-pyrrolidinyl)-cyclohexyl]-N-methylbenzeneacetamide, and salts thereof, which have been found to have useful ranges of analgesic properties while also having low apparent physical dependence properties. This invention also includes pharmaceutical compositions containing these compounds as an active analgesic component and the method of inducing analgesic activity in an animal patient, including humans, by administering one of these new compounds in an amount effective and sufficient to induce analgesic activity, regardless of origin, e.g., traumatic pain, bone pain, cancer pain, post-surgical pain, homotopic pain, menstrual pain, headache, and the like. The invention also relates to new compounds in pharmaceutical dosage unit forms to be used, hopefully more advantageously, for the relief of pain in valuable animals and human patients suffering pain.

The invention also includes a method of treating pain in a human or valuable animal mammalian patient by administering to the patient suffering pain an amount of one of these compounds effective to alleviate or minimize such pain.

DETAILED DESCRIPTION OF THE INVENTION

More particularly, this invention provides some new compounds having a chemical structure of Formula II, below, wherein p and n are each integers independently selected from the group 1, 2 and 3 so that the resulting cycloaliphatic ring of Formula II has from 5 to 7 ring carbon atoms, inclusive, and the $R_3$ and $R_4$ bearing carbon is separated from the nitrogen bearing carbons of that cycloaliphatic ring by at least one ring methylene group.

In detail, the compounds of this invention are those of the formula

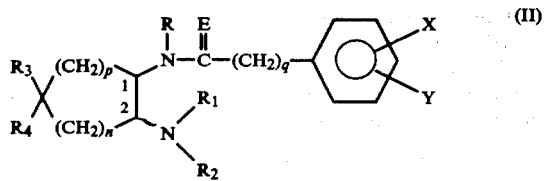

wherein
p and n are each full number integers of from 1 to 3, so that the resulting cycloaliphatic ring has five to seven carbon atoms; the wavy line bond (∼) between the nitrogen in the 2-position and the cycloaliphatic ring carbon indicates the bond can be either cis- or trans- with respect to each substituent of the cycloaliphatic ring;
q is 0 or 1;
X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino [(—NHC(O)R$_6$)];
R is hydrogen or $C_1$ to $C_3$-alkyl;
$R_1$ and $R_2$, taken separately, are hydrogen, $C_1$ to $C_3$-alkyl, allyl, or
$R_1$ and $R_2$, taken together with the nitrogen to which they are bonded, complete a ring selected from the group consisting of azetidinyl, pyrrolidinyl and piperidinyl;
$R_3$, taken separately, is hydrogen, and
$R_4$, taken separately, is mercapto (SH), —S—($C_1$ to $C_3$-alkyl), or $R_3$ is —GR$_5$ and $R_4$ is —GR$_5$;
wherein E is bivalent sulfur or oxygen;
each G is bivalent sulfur or oxygen;
$R_5$ is $C_1$ to $C_2$-alkyl;
$R_6$ is H or $C_1$ to $C_2$-alkyl;
and the acid addition salts thereof, particularly pharmaceutically acceptable salts thereof. Thus, the $R_3$, $R_4$-substituent moiety is in the 4-position of cyclopentyl ring compounds, in the 4- or 5-position of cyclohexyl ring compounds (or a mixture of compounds wherein the $R_3$ and $R_4$ substituents are on the 4- and 5-positions), and in the 4-, 5- or 6-positions of cycloheptyl ring compounds (or a mixture of such $R_3$, $R_4$ position isomers). Thus, this invention involves compounds wherein the $R_3$, $R_4$-bearing carbon is not vicinal (adjacent) to either of the nitrogen bearing carbons of that same cycloaliphatic ring.

The compounds of Formula II or their acid addition salts in their crystalline state may sometimes be isolated from their reaction mixtures as solvates, i.e., with a discrete quantity of solvent, e.g., water, ethyl acetate, methanol and the like, associated physically, and thus not affecting the chemical entity per se.

It will be recognized by those skilled in the organic chemical art that the carbon atoms at positions 1 and 2 of the cycloaliphatic ring of structure (II) to which nitrogens are bonded are asymmetrically substituted. Likewise, for certain definitions of $R_3$ and $R_4$, the cycloaliphatic ring carbon atom to which $R_3$ and $R_4$ are bonded may also be asymmetrically substituted. Each of these three carbon atoms can independently possess an R or S-configuration and thus a compound of the formula (II) may have as many as $2^3$ or 8 stereoisomers which comprise four pairs of enantiomers; each enantiomeric pair is termed a racemate. See, for example, J. B. Hendrickson, D. J. Cram, and G. S. Hammond, Organic Chemistry, Third Edition, McGraw-Hill Book Company, New York, NY, 1970, pages 198–230, particularly pages 207, 208, 213, and 215. Of the four racemates, two will have the nitrogen-containing groups at positions 1 and 2 of structure (II) in a trans orientation: that is, the groups will be on opposite sides of the plane of the cycloaliphatic ring; such compounds will be generally referred to in this specification as trans compounds. The other two racemates will have the nitrogen-containing groups at positions 1 and 2 of structure (II) in a cis orientation: that is, the groups will be on the same side of the cycloaliphatic ring; such compounds will be generally referred to in this specification as cis compounds and are meant to include both possible configurations of the third substituted ring carbon atom if it is asymmetrically substituted. The four racemates of structure (II) compounds can each exist as a mixture of the two enantiomers or each enantiomer of each pair can be separated. When it is desired to specify for a structure (II) compound the configuration of the other asymmetric center relative to that of position 1, this is done according to the Chemical Abstracts Service Publication, "Naming and Indexing of Chemical Substances for CHEMICAL ABSTRACTS during the Ninth Collective Period (1972–1976)", a reprint of Section IV (Selection of Index Names for Chemical Substances) from the CHEMICAL ABSTRACTS Volume 76 Index Guide. Accordingly, the relative stereochemistry of three asymmetric carbon atoms in the cycloaliphatic ring of Formula II compounds is indicated by: (1) the arbitrary designation of 1α for the orientation of the substituent on (asymmetric) carbon atom number one; (2) the designation 2α or 2β when the substituent on (asymmetric) carbon atom number two is on the same or opposite side of the plane of the cycloaliphatic ring, respectively, relative to said $C_1$-substituent, and (3) the designation xα or xβ when the substituent on (asymmetric) carbon atom number x is on the same or opposite side of the plane of the cycloaliphatic ring, respectively, relative to said $C_1$-substituent.

Two isomers which differ only in the stereochemistry at one asymmetric carbon atom of the cycloaliphatic ring are referred to as epimers.

In the above Formula II compounds, the halogens having atomic numbers of from 9 to 35 are fluorine, chlorine and bromine, the term "$C_1$ to $C_3$-alkyl" means methyl, ethyl, n-propyl and isopropyl, the term "$C_1$ to $C_2$-alkyl" means methyl and ethyl, and allyl means 2-propen-1-yl.

A preferred subgroup of these Formula II compounds are those
wherein
p is 1 to 3, n is 1 to 3 and p and n are selected so that the cycloaliphatic ring has 5 to 7 ring carbons, q is 0 or 1, and at least one of X and Y is a halogen having an atomic number of from 9 to 35 in the 3- or 4-positions, or both of X and Y are such halogens in the 3- and 4-positions of the phenyl ring;
R is $C_1$ to $C_3$-alkyl;
$R_1$ and $R_2$ are taken together with the nitrogen to which they are bonded to complete an azetidinyl, pyrrolidinyl or piperidinyl ring;
$R_3$ and $R_4$ are each a —$GR_5$ group, $R_5$ is $C_1$ to $C_2$-alkyl and G is oxygen, and E is oxygen, and the pharmaceutically acceptable salts thereof. Examples of compounds of this group include the cis- and trans-isomers of:
3,4-dichloro-N-[4,4-dimethoxy-2-(1-pyrrolidinyl)cyclohexyl]-N-methylbenzeneacetamide which can also be named:
3,4-dichloro-N-methyl-N-[4-oxo-2-(1-pyrrolidinyl)cyclohexyl]benzeneacetamide, dimethyl ketal,
3,4-dichloro-N-[5,5-diethoxy-2-(1-pyrrolidinyl)cyclohexyl]-N-methylbenzeneacetamide,
4-bromo-N-[4,4-dimethoxy-2-(1-pyrrolidinyl)cyclohexyl]-N-methylbenzamide,
3,4-dichloro-N-[4,4-dimethoxy-2-(1-azetidinyl)cyclopentyl]-N-ethylbenzeneacetamide,
3,4-difluoro-N-[4,4-dimethoxy-2-(1-piperidinyl)cycloheptyl]-N-methylbenzeneacetamide,
4-bromo-N-[6,6-diethoxy-2-(1-pyrrolidinyl)cycloheptyl]benzamide, and the like, and the pharmacologically acceptable salts thereof.

The di-$C_1$ to $C_2$-alkyl ketals of this invention, that is, the compounds of the Formula II wherein $R_3$ is —$GR_5$ and $R_4$ is —$GR_5$ and each G is oxygen, can be prepared by reacting a ketone of Formula XVII (Chart A below) or the analogous cis amino-amide ketone (Charts B, C, and D below) in methanol or ethanol as solvent in the presence of trimethylorthoformate or triethylorthoformate, respectively, and a suitable acid such as hydrochloric acid. The resulting reaction mixture is reacted at from 20° C. to reflux for a time sufficient to form the desired dialkyl ketal compound (II); usually a reaction time of about 16 hours in refluxing methanol or ethanol is a sufficient reaction time. The solvent is then removed by evaporation and the dialkyl ketal product (II) is purified by conventional techniques such as recrystallization or chromatography.

Alternatively the di-$C_1$ to $C_2$-alkyl ketals of this invention can be prepared by reacting a ketone of the formula XVII or the analogous cis amino-amide ketone with either methanol or ethanol in the presence of an acidic catalyst such as para-toluenesulfonic acid at a temperature up to the reflux temperature of the mixture for about 14 to 24 hours, optionally using a solvent such as benzene and azeotropically removing the water formed, to form the desired dialkyl ketal of this invention. Such a method is well known in the art: see, for example, S. M. McElvan and M. J. Curry in Journal of the American Chemical Society, Volume 70, pages 3781 and following, 1948.

The di-$C_1$-$C_2$-alkylthio ketals of this invention, that is, the compounds of the Formula (II) wherein $R_3$ is —$GR_5$, $R_4$ is —$GR_5$ and each G is sulfur can be prepared by methods well known in the art as described generally in "Protective Groups in Organic Synthesis", T. W. Greene, John Wiley & Sons, New York, 1981, pp. 129–30. Thus a ketone of the Formula (XVII) or an analogous cis ketone, is reacted with methyl or ethyl mercaptan in the presence of a suitable acid such as hydrochloric acid to form a dialkylthio ketal of this invention.

The thiols of this invention, that is, compounds of the Formula (II) wherein $R_3$ is hydrogen and $R_4$ is SH, are prepared by methods known in the art as described for example in "Comprehensive Organic Chemistry—The Synthesis and Reactions of Organic Compounds", Ed. D. Barton and W. D. Ollis, Volume 3 edited by D. N. Jones, Pergamon Press, New York, 1979, pp. 6–8. For example, an alcohol of the Formula (XVIII) (Chart A) (or an analogous cis alcohol) can be converted to a para-toluenesulfonate derivative which is reacted with hydrogen sulfide to produce the desired thiol of this invention. An additional helpful literature reference is "The Chemistry of the Thiol Group" Part 1, Ed. S. Patai, John Wiley & Sons, New York, 1974, for example, pages 163, 164, 179, 180, 220.

The monoalkylthio compounds of this invention, that is, the compounds of Formula (II) wherein $R_3$ is hydrogen and $R_4$ is —S—($C_1$ to $C_3$-alkyl), are prepared by methods known in the art as described, for example, in "Comprehensive Organic Chemistry" cited above, pages 36–39. A thiol of this invention produced as described above is reacted with an appropriate $C_1$ to $C_3$-alkyl halide, preferably bromide, to produce a monoalkylthio compound of this invention.

Throughout the synthetic procedures described herein, care must be taken that the groups X and Y are not undesirably altered by the reaction conditions. The use of protecting groups may be necessary as well known in the art.

The starting materials to prepare the new compounds of this invention (Formula II compounds above) are described in application Ser. No. 06/252,535 filed Apr. 9, 1981, now allowed. In general, and with the exceptions set forth below, these starting materials can be prepared by reacting the selected 1,2-cycloaliphatic diamine of the Formula III

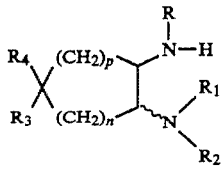

wherein p, n, R, $R_1$, $R_2$, are as defined above and $R_3$ and $R_4$, taken together, denote an —OCH$_2$CH$_3$O— (ethylene ketal) substituent with (1) a suitable acyl source such as the appropriate acyl imidazole of the formula

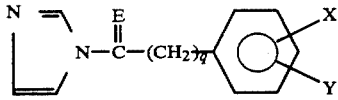

wherein q, E, X and Y are as defined above; (2) or with an acyl halide of the formula

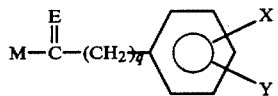

wherein M is chloride or bromide and q, E, X and Y are as defined above in the presence of an acid scavenger such as triethylamine; or (3) with the carboxylic acid of the formula

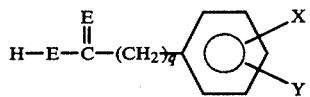

in the presence of a condensing agent, such as a carbodiimide, wherein q, E, X and Y are as defined above, in an organic solvent for the reactants, preferably in an ether solvent such as diethyl ether, or a cyclic ether solvent such as tetrahydrofuran (THF) or dioxane, or the like, until the desired amino-amide ketal compound is produced. Carbodiimides such as dicyclohexylcarbodiimide or diisopropylcarbodiimide can be used. The amino-amide ketal compound is then hydrolyzed to the amino-amide ketone compound which is a starting material to make compounds of this invention of the formula II.

The reactants (III) and (IV) or (III) and (V) or (III) and (VI) can be mixed in substantially equimolar proportions to effect formation of the desired starting ketone, but in cases where the nonpertinent amino nitrogens are protected against reaction, if one of the reactants III, IV, V and VI is more expensive than the other, it is sometimes preferred to use a stoichiometric excess of the less expensive reactant to insure that substantially all of the more expensive reactant is consumed in the reactions. The reaction will proceed at ambient temperature for most combinations of reactants, but for some combinations of reactants, variations from the initial to final reaction conditions may very between −25° C. and reflux temperature of the mixture depending on the reactivity of the reactants, the desired reaction time, the solvent being used, the molar proportions, and similar factors of concern to the chemist operating the process.

Exceptions—When the new compound of this invention is to be one of formula II in which one or both of $R_1$ and $R_2$ is to be hydrogen, the amino-hydrogens in the $R_1$ and/or $R_2$ positions must first be protected by procedures known in the art, then the N-protected diamine reactant (IIIa)

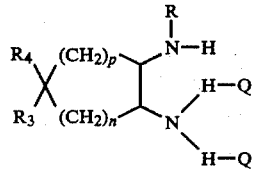

wherein R, $R_3$, $R_4$, n and p are as defined for Formula III and each "—H—Q" denotes a protected amino hydrogen group, reacted with the selected acyl imidazole IV, or with the acyl halide V, or with the carboxylic acid VI in the presence of a condensing agent, to form the N-[2-(N-protected-amino)oxy or thia-group-substituted cycloaliphatic]benzamide or benzeneacetamide, which is then treated to remove the N-protecting group to leave as product the desired N-[2-(amino)-oxo or thio- group-substituted-cycloaliphatic]benzamide or -benzeneacetamide. Under certain conditions, N-deprotection can optionally be done at a later step in the synthesis of a compound of the formula II.

Procedures for preparing the aracyl imidazoles (IV) and acyl halide (V) reactants used to form compounds of this invention are known in the art. See, for example, R. B. Wagner and H. D. Zook, SYNTHETIC ORGANIC CHEMISTRY, 1953, John Wiley and Sons, Chapter 17, p. 546 et seq. The aracyl imidazole can be prepared in situ by reacting carbonyldiimidazole with the acid of the Formula VI in an organic solvent. The carboxylic acids VI are either known in the art or are prepared by methods known in the art.

Acid addition salts can be prepared by reacting a Formula II free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, methanesulfonic, naphthalenesulfonic, p-toluenesulfonic, maleic, fumaric, oxalic acids and the like. The reaction can be carried out in aqueous or organic liquid solvent or non-aqueous media such as diethyl ether, ethyl acetate, and the like. Non-aqueous media are preferred. When it is desired to obtain optically resolved products in crystalline form, it may be more convenient to form salts such as maleates, citrates or pamoates rather than the inorganic acid addition salts, such as the hydrochlorides. Also, whereas some acids, for example oxalic acid, can be used to produce the amino-amide product in a more easily handled solid form, e.g., in plant manufacturing isolation procedures, it would preferably not be used as a pharmaceutically acceptable salt form of the amino-amide product.

Procedures for preparing the oxy-group substituted diamines (III) useful for preparing the compounds of this invention can be summarized by the chemical reaction Charts A, C and D.

The processes used to make the starting compounds of this invention are illustrated in Charts A, C, and D. In these Charts R, $R_1$, $R_2$, $R_5$, p, n, q, E, X, and Y are as defined above; b is defined in Chart A. The products of these reactions can be isolated and purified by conventional means.

Introduction of the amino protecting groups is preferably accomplished by using suitable protected amino starting materials. The choice of protecting groups should be made such that the groups X and Y are not undesirably altered by the conditions for introduction or removal of these protecting groups.

The volatility of one or more reactants may require the use of a closed reaction vessel for some of the reactions described below.

Starting materials of the formulas (XVI) and (XVII), for making compounds of this invention are prepared using the process steps illustrated in Chart A. A suitable keto alcohol of the formula (VIIa) is reacted with an appropriate glycol and a catalytic amount of an acid such as p-toluenesulfonic acid with azeotropic removal of water to afford a hydroxy ketal of the formula (VII). Alternatively, reduction of a suitable compound of the formula (VIII) with a suitable reducing agent such as lithium aluminum hydride in a suitable solvent such as diethyl ether or tetrahydrofuran gives a hydroxy ketal of the formula (VII). Reaction of a hydroxy ketal compound of the formula (VII) with p-toluenesulfonyl chloride in pyridine yields a sulfonate ester of the formula (IX), which sulfonate ester is reacted with a suitable base such as 1,5-diazabicyclo[4.3.0]non-5-ene (DBN) to produce an alkene of the formula (X). An alkene compound of the formula (X) is oxidized with an organic peracid such as metachloroperbenzoic acid in a suitable solvent such as methylene chloride to generate an epoxide of the formula (XI). An epoxide of the formula (XI) is reacted with an amine of the formula, $R'NH-R_7$, which amine can be used in excess and thus also serve as the reaction medium, optionally in the presence of water, at elevated temperature for a sufficient time to form an amino alcohol of the formula (XII). In some instances the opening of the epoxide to produce a compound of the formula (XII) proceeds such that one of the possible isomeric trans products of the formula (XII) is the predominate or exclusive product of the reaction. Reaction of an amino alcohol of the formula (XII) with methanesulfonyl chloride in the presence of a suitable acid scavenger such as triethylamine in a suitable organic solvent such as methylene chloride, preferably with external cooling, followed by reaction of the resulting compound with an amine of the formula, $HNR'_1R'_2$, which may be taken in excess and thus serve as the reaction medium, optionally in the presence of water, at elevated temperature for a sufficient time provides a mixture of two diamines of the formula (XIII), each having interchanged values of p and n relative to the other. (It is recognized that when p is equal to n, only one compound of the formula (XIII) is obtained.) Alternatively, when one of R' and $R_7$ is hydrogen, reaction of an amino alcohol of the formula (XII) with methanesulfonyl chloride, as described above, and then reaction of the resulting compound with aqueous sodium hydroxide at elevated temperature, affords an aziridine of the formula (XIV) which aziridine is reacted with an amine of the formula $HNR'_1R'_2$, as described above, to give a mixture of two diamines of the formula (XIII), each having interchanged values of p and n relative to the other.

Reaction of an epoxide of the Formula (XI) with an amine of the Formula $HNR'_1R'_2$, as described above, gives an amino alcohol of the Formula (XV). In some instances the opening of the epoxide to produce an amino alcohol compound of the formula (XV) proceeds such that one of the possible isomeric trans products of the formula (XV) is the predominate or exclusive product of the reaction.

An amino alcohol of the formula (XV) is reacted with methanesulfonyl chloride, as described above, followed by reaction of the resulting product with an amine of the Formula $R'NH_2$, which may be taken in excess and thus serve as the reaction medium, optionally in the presence of water, at elevated temperature for a time sufficient to form a mixture of two diamines of the Formula (XIII), each having interchanged values of p and n relative to the other.

A diamine of the Formula (XIII) is reacted with a suitable acyl source as described above to produce an amino amide of the Formula (XVI). An amino amide of the Formula (XVI) is reacted with an aqueous mineral acid such as hydrochloric acid to give a ketone of the Formula (XVII). Reduction of a ketone of the Formula (XVII) with K-Selectride (potassium tri-sec-butylborohydride) in a suitable organic solvent such as tetrahydrofuran, preferably at low temperature, ($-75°$ to $0°$ C.) provides one hydroxy compound or two hydroxy compounds of the Formula (XVIII) wherein one particular epimer at the hydroxyl-bearing cycloalkyl ring carbon atom usually is the more abundant or exclusive alcohol product. Alternatively, reduction of a ketone of the Formula (XVII) with sodium borohydride in a suitable solvent, such as ethanol at about $0°$ to $25°$ C., gives one compound or two compounds of the Formula (XVIII), wherein the more abundant or exclusive alcohol product usually is the epimer opposite in configuration to that obtained from the K-Selectride reduction described above. A ketone of the Formula (XVII) is converted to a dialkyl ketal compound of this invention of the Formula (IIa) as described above.

In Charts A, C, and D, R' is R or a suitable nitrogen protecting group; $R'_1$ is $R_1$ or a suitable nitrogen protecting group; $R'_2$ is $R_2$ or a suitable nitrogen protecting group; $R_7$ is hydrogen or a suitable nitrogen protecting group. Examples of suitable nitrogen protecting groups are: (1) benzyl ($C_6H_5-CH_2-$); (2) triphenylmethyl (trityl, $(C_6H_5)_3C$); (3) para-toluenesulfonyl ($p-CH_3-C_6H_4-SO_2-$); and (4) trialkylsilyl, for example, trimethylsilyl (($CH_3)_3Si-$) or tertiary butyldimethylsilyl (($CH_3)_3CSi(CH_3)_2-$); (5) tert-butyloxycarbonyl and the like. Introduction and removal of such nitrogen protecting groups are well known in the art of organic chemistry: see, for example, (1) J. F. W. McOmie, Advances in Organic Chemistry, Vol. 3, pages 191–281 (1963); (2) R. A. Boissonas, Advances in Organic Chemistry, Vol. 3, pgs. 159–190 (1963); (3) "Protective Groups in Organic Chemistry", J. F. W. McOmie, ed., Plenum Press, New York, 1973, pg. 74.

The requisite hydroxycycloalkanones of Formula (VIIa) in Chart A are known in the art and are thus suitable starting materials for the processes outlined in Chart A. In addition, some of the keto ketals of the Formula (VIII) and some of the hydroxy ketals of the Formula (VII) are known in the art; those which are not known are prepared from compounds of the formula (VI) by well known methods. The amines of the Formulas $R'NHR_7$ and $HNR'_1R'_2$ are either known in the art or prepared by standard methods.

Under certain circumstances it is necessary to protect two different nitrogens with different protecting groups such that one such protecting group can be selectively removed while leaving the second protective group in place. The trityl and benzyl protecting groups can be used in this way, the trityl group being removable in the presence of the benzyl group under acidic conditions. Likewise, the tert-butyloxycarbonyl and benzyl groups can be used in this way.

The requirements for protective groups in Charts A, C, and D are generally well recognized by one skilled in the art of organic chemical synthesis, and the use, when required, of the appropriate protecting group or groups is indicated in Charts A, C, and D by the use of the symbols R′, R′$_1$, R′$_2$, and R$_7$; removal of a protecting group is implied when R′, R′$_1$, R′$_2$ or R$_7$ is replaced in a subsequent formula by R, R$_1$, R$_2$, or H, respectively; N-protected compounds can be deprotected as desired by known methods at appropriate points in the synthesis.

Cis dialkyloxy compounds of Formula II can be prepared as shown in Chart B. The cis-amino-amide ketone starting material is prepared as described in Charts C or D. The cyclic ketal compound XXXVII in Chart C is converted to the ketone (XXV) by the procedures described above.

A compound of Formula II, wherein at least one of X and Y is hydroxyl, is prepared as follows: A suitable ketone of Formula (XVII), wherein X and/or Y is methoxy, is reacted with boron tribromide in methylene chloride to produce a ketone of the Formula (XVII) wherein the corresponding X and/or Y is hydroxyl, which hydroxyl compound can be further reacted as in Chart A.

According to Chart C, reaction of a ketone of the Formula (VIII) with a suitable base such as sodium hydride in a suitable inert organic solvent such as DMF, followed by addition to the mixture of a lower alkyl chloroformate affords a keto ester of the Formula (XXXI), which is reacted with an amine of the formula, HNR′$_1$R′$_2$, with azeotropic removal of water to produce an enamine of the Formula (XXXII). Alternatively, a ketone of the Formula (VIII) is converted to an enamine of the Formula (XXXIII), which enamine is reacted with a lower alkyl chloroformate to give an enamine of the formula (XXXII). Hydrogenation of an enamine of the Formula (XXXII) with hydrogen and a suitable catalyst such as platinum (from platinum oxide) in a suitable organic solvent such as ethyl acetate or a lower alkanol yields a cis amino ester of the Formula (XXXIV). Reaction of an amino ester of the formula (XXXIV) with a suitable base such as an alkali metal hydroxide, for example, sodium or potassium hydroxide, followed by a Curtius reaction affords a diamine of the formula (XXXV). The Curtius reaction is conducted as described by P. W. Erhardt, J. Org. Chem., 44, 883 (1979)! or as described by T. Shioiri, et al., J. Amer. Chem. Soc.(94, 6203 (1972) or the like. If R of a Formula II compound being prepared is C$_1$ to C$_3$-alkyl, then a diamine compound of the formula (XXXV) is alkylated with a lower alkyl halide of the formula R-Z (wherein Z is Cl, Br or I) or acylated with an appropriate acid chloride, acid anhydride or mixed anhydride in a suitable medium such as pyridine optionally at elevated temperature, followed by diborane reduction according to H. C. Brown and P. Heim, J. Amer. Chem. Soc., 86, 3566 (1964), to generate a diamine of the Formula (XXXVI). Reaction of a diamine of the Formula (XXXVI) with a suitable acyl source as described above yields a compound of the Formula (XXXVII) which can be converted to a ketone of the Formula (XXV) as described above. When one or both of R$_1$ and R$_2$ of a cis Formula II compound being prepared using Chart C are to be allyl, suitable N protecting groups are used and the allyl group or groups must be introduced after the enamine hydrogenation step. To prepare additional cis Formula II compounds of this invention, a compound of the Formula (XXXVII) is analogously reacted: (1) as described in Chart A for the conversion of a compound of the Formula (XVI) to compounds of the Formulas (XVII), (XVIII), and (IIa); and (2) as described elsewhere in this specification for a compound of the Formula (XVII).

In addition, some of these cis compound starting materials of the Formula (XXV) are also prepared using an alternate process to produce a diamine of the Formula (XXXVI) as illustrated in Chart D. As described for Chart A, an epoxide of the Formula (XI) is prepared and converted to an amino alcohol of the Formula (XII), which is oxidized using standard methods, for example, chromium trioxide (CrO$_3$)-sulfuric acid in acetone solvent at 0° C. (Known as the Jones oxidation) or chromium trioxide-pyridine, to afford a ketone of the Formula (XXXVIII). A ketone of the Formula (XXXVIII) is reacted with an amine of the formula H$_2$NR′$_1$ in the presence of magnesium sulfate (MgSO$_4$) in a suitable organic solvent such as benzene to produce an imine of the Formula (XXXIX). An imine of the Formula (XXXIX) is reduced with a suitable reducing agent such as lithium aluminum hydride (LiAlH$_4$) or sodium cyanoorohydride (NaBH$_3$CN) to give a cis diamine of the Formula (XL) admixed with the corresponding trans diamine. The reduction of imines with these reagents is described by D. A. Evans et al.,. J. Amer. Chem. Soc., 100, 8170 (1978). The cis diamine of structure (XL) is separated from the trans isomer at this stage of the synthesis or a separation is performed at a later stage, for example, after the formation of a cis benzeneacetamide or benzamide compound of the Formula (XXXVII) admixed with the corresponding trans isomer of the Formula (XVI).

When R$_2$ of a Formula (II) compound being prepared is other than hydrogen, or when R$_1$ and R$_2$ of a Formula II compound being prepared, taken together with the nitrogen to which they are bonded complete an azetidinyl, pyrrolidinyl or piperidinyl ring, such nitrogen substitution is introduced at this stage of the synthesis using an alkylation of a diamine of the Formula (XL), amine alkylations being well known in the art, to produce an alkylated diamine compound of the Formula (XLI). An alkylated diamine of the Formula (XLI) is deprotected to give a diamine of the formula (XXXVI) which is treated with a suitable acyl source as described above to afford a compound of the Formula (XXXVII). A ketal of the Formula (XXXVII) is hydrolyzed to a ketone of the Formula (XXV) as described above.

As an alternative to procedures described above, the group B in Charts A, B and D can be a dialkyl ketal rather than an ethylene ketal. The required dialkyl ketal starting materials are prepared by methods known in the art. Using this modification in Chart A, compounds of the formula XVI are compounds of this invention, wherein B represents a carbon atom bearing two C$_1$ and C$_2$-alkoxy groups. The dialkyl ketal compounds thus produced can be used for its analgesic effects as described in this specification, or it can be used as a chemical intermediate which, when hydrolyzed as described above, yields a ketone of the formula XVII.

The term "dosage unit form" as used in this specification and in the claims refers to physically discrete units suitable as uitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in this specification, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc, and the like. Capsules, both hard and soft, are filled with compositions of these amino-amide active ingredients in combination with suitable diluents and excipients, for example, edible oils, talc, calcium carbonate and the like, and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferably to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to about 350 mg of the essential active ingredient per dosage unit form, which as aforesaid may be in the form of a semi-solid or solid, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain analgesic effects within the aforesaid effective non-toxic range. Expressed otherwise, when used systemically, an amount of the essential active ingredient is provided to a recipient within a range from about 0.01 mg per kg to about 5 mg of the Formula II compound per kg of body weight of the recipient. Preferred dosages for most applications are 0.05 to 2.0 mg per kg of body weight.

The useful pharmaceutical dosage unit forms of these compounds in pharmaceutical formulations are preferably adapted for systemic administration to obtain analgesic effects comprising an effective, nontoxic amount of a compound according to Formula II or as its pharmacologically acceptable salt.

Further, the invention relates to methods of obtaining analgesic effects in mammals, for example, humans and valuable warm-blooded animals such as dogs, cats, horses and other commercially valuable animals, by administering systemically to the mammals the aforesaid pharmaceutical dosage unit forms supplying an effective, non-toxic amount for analgesic effects. These preferred compounds have an advantage, to a greater extent, depending upon the particular compound, of having lower physical dependence liability than known analgesic compounds such as morphine and methadone, as shown by evaluation of representative compounds and those standard analgesic drug compounds in various pharmacological test procedures which measure analgesia and the physical dependence liability of the test compounds in standard laboratory test animals.

Representative examples of these Formula II compounds have $ED_{50}$ values of less than about 75 mg/kg s.c. (subcutaneous administration) in standard laboratory animal analgesic tests such as the tail flick, pinch, and hydrochloric acid writhing tests, and the more potent of them have $ED_{50}$ values of less than 10 mg/kg (s.c.) in these tests. The procedures used to determine these properties of these new compounds were essentially those of Way et al., (Way, E.L. et al., "Simultaneous Quantitative Assessment of Morphine Tolerance and Physical Dependence", J. Pharmacol. Exp. Ther., 167, pp. 1–8 (1969)) and Saalens et al., (Saalens, J. K. et al., "The Mouse Jumping Test—A Simple Screening Method to Estimate the Physical Dependence Capacity of Analgesics", Arch. Int. Pharmacodyn., 190, pp. 213–218 (1971)). Statistical effective doses ($ED_{50}$ values) and 95% confidence limits were calculated by the method of Spearman and Karber (Finney, D. J., "Statistical Methods in Biological Assay", Hafner Publ., (1952)).

The invention is further exemplified by the following detailed examples, the procedures of which can be used to prepare compounds of this invention, but these examples are not intended to limit the scope of the invention. All temperatures are in degrees centigrade unless otherwise noted. For brevity, Hg means mercury, bp means boiling point, IR (or ir) means infrared spectrum points of reference, m/e means the mass of a mass spectral fragment divided by its charge, M+ means the mass corresponding to the parent molecular ion, $CH_2Cl_2$ means methylene chloride solvent, $K_2CO_3$ or $Na_2SO_4$ means the organic layer was dried over anhydrous forms of these salts, mp means melting point, NMR (or nmr) means nuclear magnetic resonance spectrum and NMR ($CDCl_3$) means a nuclear magnetic resonance spectrum made using deuteriochloroform as a solvent and values in parts per million are reported as downfield shifts from a tetra-methylsilane internal reference; DBN means 1,5-diazabicyclo[4.3.0]non-5-ene; h means hour(s), $N_2$ means nitrogen, tlc means thin layer chromatography procedures, Na$_2$SO$_3$ means sodium sulfite, NaHCO$_3$ means sodium bicarbonate, DMSO is dimethylsulfoxide, Skellysolve B (or Skelly B) is a tradename for a solvent of essentially n-hexane, bp 60°–68° C. (Merck Index, Ninth Edition (1976), page 1106), Et$_2$O means diethyl ether, MeOH means methanol, THF means tetrahydrofuran, H$_2$O means water, CHCl$_3$ means chloroform, brine is saturated aqueous sodium chloride solution, DMF means N,N-dimethylformamide, Et$_3$N is triethylamine, HRMS means high resolution mass spectrum, EtOAC means ethyl acetate; HCl means hydrogen chloride.

PREPARATION 1

Preparation of
trans-3,4-dichloro-N-methyl-N-[8-(1-pyrrolidinyl)-1,4-dioxaspiro[4.5]dec-7-yl]benzeneacetamide and
trans-3,4-dichloro-N-methyl-N-[7-(1-pyrrolidinyl)-1,4-dioxaspiro[4.5]dec-8-yl]benzeneacetamide

A. 8-Hydroxy-1,4-dioxaspiro[4.5]decane

A mixture of 4hydroxycyclohexanone (228 g, 2.0 mol) ethylene glycol (124 g, 2.0 mol) and p-toluenesulfonic acid monohydrate (0.89 g) in 2.0 l of benzene was stirred at reflux in a 3-l, three-necked, round-bottomed flask equipped with a Dean-Stark trap. The mixture was refluxed until the required amount of water had been removed. Solvent was removed by distillation and the residue was fractionally distilled at 85°–88.5° C. (0.08 mm Hg.) to give 247.8 g of the sub-titled intermediate. (78%), Lit bp 90°–95° C. (0.2 mm Hg.). (M. K. Batuev, et al., Ixvest. Akad. Nauk S.S.S.R., Otdel, Khim Nauk, 1960, 538–549.) IR, OH (3420), C—O (1105, 1035, 920); Mass Spectrum, m/e 158 (M+).

Anal. Calcd. for C$_8$H$_{14}$O$_3$: C, 60.74; H, 8.92. Found: C, 60.28; H, 9.23.

B. 8-Tosyloxy-1,4-dioxaspiro[4.5]decane

A mixture of 8-hydroxy-1,4-dioxaspiro[4.5]decane (237 g, 1.5 mol) and 700 ml of pyridine was stirred at 0° C. while p-toluenesulfonyl chloride was added portion-wise. After the addition was completed the mixture was stirred for two days at 7° C. The mixture was poured into a 4-kg mixture of equal parts of ice and water with vigorous stirring. After about fifteen minutes a solid separated; this was filtered and washed with water. Dissolved the solid in CH$_2$Cl$_2$ and separated CH$_2$Cl$_2$ solution from residual water. The organic layer was dried (K$_2$CO$_3$—Na$_2$SO$_4$), filtered and concentrated in vacuo at 36° C. The solution remaining was diluted with Skellysolve B and cooled to −75° C. with stirring. The white solid was filtered and dried in vacuo to give 435 g (92.9%), mp 65°–67.5° C. of the subtitled intermediate. IR C═C (1600), —SO$_2$O— (1350, 1180), C—O/S—O—C (1105, 945, 925), —SO$_3$— (675); nmr (CDCl$_3$) was in accordance with the structure assignment; mass spectrum m/e 312 (M+).

Anal. Calcd. for C$_{15}$H$_{20}$SO$_5$: C, 57.67; H, 6.45; S, 10.27. Found: C, 57.06; H, 6.30; S, 10.17.

C. 1,4-Dioxaspiro[4.5]dec-7-ene

Method A. 8-Tosyloxy-1,4-dioxaspiro[4.5]decane (62.4 g, 0.2 mol) was added portion-wise to diazabicyclo[4.3.0]non-5-ene (DBN) (27.3 g, 0.22 mol) at ambient temperature. When the addition was completed the suspension was heated to 89° C. and the heat source was removed. The reaction temperature continued to rise and reached 116° C. before it began to fall. The mixture was stirred at 100° C. for one hour and forty-five minutes before cooling the mixture, diluting with water, and extracting with hexane. The hexane extracts were washed with 100 ml of saturated salt solution, dried (Na$_2$SO$_4$), and concentrated to a light yellow liquid. The crude olefin weighed 21 g (75%), distillation at reduced pressure gave 15.15 g (54%) of the sub-titled olefin at 111.5°–113° C./25 mm. IR, ═CH (3020), C═C (1655), C—O (1110, 1060, 1030); nmr (CDCl$_3$) was in accordance with the structure assignment; mass spectrum m/e 140 (M+).

Anal. Calcd. for C$_8$H$_{12}$O$_2$: C, 68.54; H, 8.63. Found: C, 68.62; H, 8.91.

Method B. A mixture of 8-tosyloxy-1,4-dioxaspiro[4.5]decane (20.8 g, 0.067 mol), sodium bicarbonate (6.5 g, 0.077 mol), and 100 ml of DMSO was stirred at 95° C. for 20 h under N$_2$ diluted with 100 ml of water and extracted with 3×200 ml of Skellysolve B. The extracts were washed with 100 ml of water, dried (Na$_2$SO$_4$), and concentrated in vacuo to a pale yellow liquid, 6.9 g (74%). The material (subtitled olefin) was nearly pure by tlc and nmr analyses and identical to olefin prepared as by Method A.

D. Spiro[7-oxabicyclo[4.1.0]heptane-3,2'-[1,4]-dioxolane]

m-chloroperoxybenzoic acid (85%, 32.9 g, 0.163 mol) in 418 ml of CH$_2$Cl$_2$ was added dropwise to a stirred and cooled (−5° to 0° C.) mixture of 1,4-dioxaspiro[4.5]dec-7-ene (21.2 g, 0.151 mol) in 150 ml of CH$_2$Cl$_2$ was stirred for three days at ambient temperature. A 10% solution of Na$_2$SO$_3$ (111 ml) was added dropwise to the ice-cooled mixture until a negative test with starch-iodide paper indicated no peracid was present. The insoluble benzoic acid was removed by filtration and the mixture was extracted with 250 ml of 6% NaHCO$_3$, washed with brine, and dried (Na$_2$SO$_4$). Removal of solvent in vacuo gave 24.7 g of nearly pure material (the sub-titled epoxy compound). Distillation of the liquid at 54°–56° C./0.1 mm Hg. gave 17.6 g (74.8%) of this material as a clear liquid. Nmr (CDCl$_3$) is in accordance with the structure assignment and the mass spectrum indicates a fragment at m/e 155 (M+−1).

Anal. Calcd. for C$_8$H$_{12}$O$_3$: C, 61.52; H, 7.75. Found: C, 61.48; H, 8.08.

E. trans-8-Hydroxy-7-(methylamino)-1,4-dioxaspiro[4.5]-decane

A mixture of spiro[7-oxabicyclo[4.1.0]heptane-3,2'-[1,4]dioxolane] (101 g. 0.65 mol) and 40% aqueous methylamine (151 g, 1.94 mol) was stirred at ambient temperature for forty-eight hours, then heated on a steam bath for two hours. The mixture was cooled with an ice-water bath while being saturated by addition of solid NaOH. A dark upper layer separated from the mixture and this was removed. The aqueous layer was extracted with CHCl$_3$ and the CHCl$_3$ was dried (Na$_2$SO$_4$) and concentrated in vacuo to a dark liquid. Distillation at 115°–117° C./0.35 mm Hg. gave 89 g (73.5%). Distillation of the residue on a Kugelrohr apparatus at 105° C./0.3 mm Hg. gave an additional 12.6 g (10.4%). Total yield of the subtitled amine product is 83.9%. Mass spectrum m/e 187 (M+), nmr, and ir are consistent with the structure assignment.

Anal. Calcd. for C$_{19}$H$_{17}$NO$_3$: C, 57.73; N, 9.15; N, 7.48. Found: C, 57.51; N, 9.08; N, 7.51.

F.
7-Methylspiro[7-azabicyclo[4.1.0]heptane-3,2'-[1,4]-dioxolane]

A mixture of trans-8-hydroxy-7-(methylamino)-1,4-dioxaspiro-[4.5]decane (141.9 g, 0.76 mol) in 2.5 l of $CH_2Cl_2$ was stirred under $N_2$ atmosphere at $-8°$ to $-4°$ C. while chlorosulfonic acid (49.4 ml, 88.4 g, 0.76 mol) was added dropwise. The cooling bath was removed after the addition was completed and the mixture was stirred at ambient temperature for two days. The flask was modified for distillation and $CH_2Cl_2$ was removed on a steam bath. Aqueous sodium hydroxide (1.1 N, 1.5 l) was added and the mixture was stirred and heated on a steam bath for twenty-seven hours. The cooled solution was extracted extensively with $CHCl_3$ and the extracts were washed successively with liter portions of water and saturated NaCl solution. Removed the solvent on a rotary evaporator and distilled at reduced pressure to give 61 g (49.6%) of the liquid subtitled product at 46.5°–52° C./0.05–0.065 mm Hg. Mass spectrum m/e 169 (M+), nmr, and ir are consistent with the structure assignment.

Anal. Calcd. for $C_9H_{15}NO_2$: C, 63.86; H, 8.94; N, 8.28. Found: C, 63.21; H, 9.22; N, 8.35.

G.
trans-7-(N-methylamino)-8-(1-pyrrolidinyl)-1,4-dioxaspiro[4.5]decane and trans-8-(N-methylamino)-7-(1-pyrrolidinyl)-1,4-dioxaspiro[4.5]decane Method A. A mixture of 7-methylspiro[7-azabicyclo[4.1.0]heptane-3,2'-[1,4]dioxolane] (28 g, 0.166 mol), pyrrolidine (56 ml, 47.6 g, 0.67 mol), ammonium chloride (0.56 g), and water (35 ml) was refluxed for a total of fifty-nine hours under $N_2$ atmosphere. The mixture was cooled in an ice-water bath and saturated with NaOH pellets. Extraction of the mixture with $CHCl_3$ and removal of $CHCl_3$ in vacuo gave 45.4 g of crude product contaminated with residual pyrrolidine. Distillation at reduced pressure gave 35.3 g (88%) of the subtitled isomer mixture material at 102°–104° C./0.02 mm Hg. Mass spectrum indicates an ion fragment at m/e 240 (M+). Nmr and ir spectra are consistent with the structure assignment.

Anal. Calcd. for $C_{13}H_{24}N_2O_2$: C, 64.96; H, 10.06; N, 11.66. Found: C, 63.64; H, 9.96; N, 11.32.

Method B. Spiro[7-oxabicyclo[4.1.0]heptane-3,2'-[1,4]dioxolane] was reacted with methyl(phenylmethyl)amine in the presence of water at 90° C. to give a 92% yield of trans-7-[methyl(phenylmethyl)amino[1,4]dioxaspiro[4.5]decan-8-ol, bp 158°–161° C. (0.005 mm Hg). This amino alcohol was reacted with methanesulfonyl chloride in the presence of triethylamine in methylene chloride solution at 0° C. and the resulting sulfonate ester was reacted with pyrrolidine in the presence of water at 90° C. to give a mixture of diamines, which were debenzylated by hydrogenation using a palladium on carbon catalyst to give a mixture (approximately 1:1 by nmr) of the subtitled diamines. The yield is 74% from the starting amino alcohol.

H.
trans-3,4-dichloro-N-methyl-N-[8-(1-pyrrolidinyl)-1,4-dioxaspiro[4.5]dec-7-yl]benzeneacetamide (Isomer 1) and trans-3,4-dichloro-N-methyl-N-[7-(1-pyrrolidinyl)-1,4-dioxaspiro[4.5]dec-8-yl]-benzeneacetamide (Isomer 2)

Method A. A mixture of trans-7-(N-methylamino)-8-(1-pyrrolidinyl)-1,4-dioxaspiro[4.5]decane and trans-8-(N-methylamino)-7-(1-pyrrolidinyl)-1,4-dioxaspiro[4.5]decane (64 g, 0.28 mol), triethylamine (39 ml, 28.3 g, 0.28 mol) and 280 ml of ether was added dropwise to a solution of 3,4-dichlorophenylacetyl chloride (65.7 g, 0.29 mol) in 280 ml of ether. The mixture was stirred for sixty-four hours and quenched by dropwise addition of water. The mixture was neutralized by addition of 60 ml of 10% NaOH solution and extracted with $CHCl_3$. The combined organic extracts were washed with water, dried ($Na_2SO_4$), and concentrated in vacuo to give an oil (147 g). The oil was dissolved in $CHCl_3$, diluted with $Et_2O$, and refrigerated to give 37 g of nearly pure Isomer 1 compound, the more polar amide. Recrystallization of this material from $CHCl_3$—$Et_2O$ gave 17.4 g, mp 93°–95° C. of Isomer 1 compound and 19.1 g of an oil. The oil was combined with the original filtrates and the mixture chromatographed over 5 kg of $SiO_2$ with $NH_4OH:MeOH:CH_2Cl_2$ (0.25:1.1:98.65%) to give 12.7 g (10.6%), mp 91°–94° C. of Isomer 2 compound which was recrystallized from $Et_2O$—Skellysolve B. An additional 9.7 g of Isomer 1 was obtained giving a total of 27.1 g (22.5%). Impure fractions were set aside for later purification. Isomer 2 had mass spectrum m/e 427/429 (M+1, chlorine isotopic peaks). Nmr and ir spectra were consistent with the structure assignment.

Anal. Calcd. for $C_{21}H_{28}Cl_2N_2O_3$: C, 59.02; H, 6.60; Cl, 16.59; N, 6.56. Found: C, 59.03; H, 6.48; Cl, 17.07; N, 6.59.

Isomer 1 had mass spectrum m/e 426/428 (M+, chlorine isotopic peaks). Nmr and ir spectra were consistent with the structure assignment.

Anal. Calcd. for $C_{21}H_{28}Cl_2N_2O_3$: C, 59.02; H, 6.60; Cl, 16.59; N, 6.56. Found: C, 59.33; H, 6.57; Cl, 17.12; N, 6.69.

Method B. As an alternative to Method A, above, a mixture of the diamines (24.7 g) prepared as described in Part G above was reacted with 3,4-dichlorophenylacetyl imidazolide (from 3,4-dichlorophenylacetic acid and N,N'-carbonyldiimidazole) in tetrahydrofuran at 20°–25° C. to give a mixture of the titled amino amides. Fractional crystallization of the crude product from diethyl ether-hexane mixture afforded 10.2 g of Isomer 1, 9.0 g of Isomer 2, and 11.0 g of a mixture of Isomers 1 and 2. The amino amides produced by this Method were identical to those produced in Method A above.

PREPARATION 2
Preparation of trans-3,4-dichloro-N-methyl-N-[4-oxo-2-(1-pyrrolidinyl)cyclohexyl]benzeneacetamide A mixture of trans-3,4-dichloro-N-methyl-N-[7-(1-pyrrolidinyl)-1,4-dioxaspiro[4.5]dec-8-yl]benzeneacetamide (12.3 g, 0.029 mol) 3N HCl solution (288 ml), and 432 ml of acetone was stirred at 60° C. under $N_2$ atmosphere for one hour. Acetone was removed on a rotary evaporator and the mixture was extracted with chloroform. The chloroform extracts were dried ($Na_2SO_4$), concentrated in vacuo and diluted with ether. Refrigeration overnight gave white crystals which were dried at 60° C. in vacuo for two days to give 10.5 g (87%) of the titled compound, mp 148.0°-148.9° C. The mass spectrum indicated ion fragments at m/e 382-384 (M+, chlorine isotopic peaks). The ir and nmr spectra were consistent with the structure assignment.

Anal. Calcd. for $C_{19}H_{24}Cl_2N_2O_2$ HCl: C, 54.36; H, 5.76; Cl, 25.34; N, 6.67. Found: C, 53.85; H, 6.19; Cl, 25.39; N, 7.02.

PREPARATION 3

(1α,2β,4α)-3,4-Dichloro-N-methyl-N-[4-hydroxy-2-(1-pyrrolidinyl)cyclohexyl]benzeneacetamide hydrochloride Trans-3,4-dichloro-N-methyl-N-[4-oxo-2-(1-pyrrolidinyl)cyclohexyl]benzeneacetamide hydrochloride (8.4 g, 0.0198 mol) was suspended in 160 ml of dry tetrahydrofuran in a three-necked, R.B. flask inerted with $N_2$ and the suspension was cooled to −78° C. A solution of 160 ml of 0.25M. potassium tri-sec-butyl-borohydride in tetrahydrofuran was added dropwise to the suspension at −78° C. When the addition was completed the cooling bath was removed and the mixture was stirred for 2.5 hours. $O_2$-free MeOH (20 ml) was added followed by addition of 20 ml of $O_2$-free $H_2O$. The mixture was acidified by addition of 180 ml of 2.5N HCl solution. Extracted the mixture with diethyl ether and backwashed the ether extracts with $H_2O$. The aqueous phases were combined and extracted with $CHCl_3$ (8×250 ml). The $CHCl_3$ extracts were washed with 250 ml of brine and dried ($Na_2SO_4$). Evaporation of solvent in vacuo gave the subtitled salt as an off-white solid (8.1 g). The solid was crystallized from $CHCl_3$—MeOH, $CHCl_3$—EtOH—$Et_2O$, and EtOH—$Et_2O$ to give three crops of solid weighing 2.5, 3.7, and 0.4 g, respectively. Combined yield of the three crops was 78.5% of the subtitled compound, m.p. 238.9°-244.9° C. Mass spectrum m/e 384/386 (M+, chlorine isotopic peaks). IR, OH (3320cm/1), NH+ (2640), C=O (amide, 1645) and nmr spectra were consistent with the structure assignment for the titled hydroxy compound.

Anal. Calcd. for $C_{19}H_{26}Cl_2N_2O_2$ 1 1HCl: C, 53.63; H, 6.16; Cl, 25.83; N, 6.59. Found: C, 53.61; H, 6.44; Cl, 25.79; N, 6.88.

EXAMPLE 1

Preparation of (±),-(1α,2β)-3,4-dichloro-N-[4,4-dimethoxy-2-(1-pyrrolidinyl)cyclohexyl]-N-methylbenzeneacetamide and its monohydrochloride hemihydrate forms To a solution of 1.0 g (2.4 millimoles) of (±)-(1α,2β)-3,4-dichloro-N-methyl-N-[4-oxo-2-(1-pyrrolidinyl)cyclohexyl]benzeneacetamide, monohydrochloride, prepared generally as described in Preparation 2 above, in 50 ml of dry methanol there was added 5 ml of trimethylorthoformate and 0.5 ml of 4M methanolic hydrogen chloride. The resulting mixture was refluxed for about 16 hours, cooled, and the solvent was removed in vacuo. The residual oil was crystallized from a hot methanol solution thereof, diluted with diethyl ether until the mixture became cloudy, to give 0.52 g (46% yield) of the titled product as white crystals, mp 128°-130° C.; mass spectrum m/e 170

$((CH_3O)_2C=CH=N(CH_2)_3CH_2)$.

Anal. Calcd. for $C_{21}H_{30}N_2O_3Cl_2$ HCl 0.5$H_2O$ C, 53.11; H, 6.79; N, 5.90; Cl, 22.40. Found: C, 53.27; H, 6.64; N, 6.23; Cl, 22.99.

EXAMPLE 2

(±)-(1α,2β)-4-bromo-N-[4,4-diethoxy-2-(1-azetidinyl)cyclohexyl]-N-methylbenzamide Following the procedure of Example 1, but substituting (±)-(1α,2β)-4-bromo-N-methyl-N-[4-oxo-2-(1-azetidinyl)cyclohexyl]benzamide for the (±)-(1α,2β)-3,4-dichloro-N-methyl-N-[4-oxo-2-(1-pyrrolidinyl)cyclohexyl]benzeneacetamide, and triethylorthoformate for the trimethylorthoformate in 50 ml of dry ethanol instead of methanol, there is obtained as product (±)-(1α,2β)-4-bromo-N-[4,4-diethoxy-2-(1-azetidinyl)cyclohexyl]-N-methylbenzamide.

Other representative compounds within the scope of the invention which can be prepared by procedures described in this specification are the cis and trans isomers of:

a.  4-trifluoromethyl-N-[4,4-dimethoxy-2-(1-pyrrolidinyl)cyclohexyl]-N-methylbenzeneacetamide,
b.  3-trifluoromethyl-N-[4,4-diethoxy-2-(1-pyrrolidinyl)cyclohexyl]-N-methylbenzeneacetamide,
c.  4-chloro-N-[4,4-dimethoxy-2-(1-azetidinyl)cyclohexyl]-N-methylbenzamide,
d.  4-fluoro-N-[5,5-diethoxy-2-(1-piperidinyl)cycloheptyl]-N-ethylbenzeneacetamide,
e.  4-nitro-N-[5,5-dimethoxy-2-(1-pyrrolidinyl)cycloheptyl]-N-(n-propyl)benzamide,
f.  4-amino-N-[4,4-dimethoxy-2-(1-azetidinyl)cyclopentyl]-N-methylbenzeneacetamide,
g.  3-hydroxy-4-methyl-N-[4,4-dimethoxy-2-(1-pyrrolidinyl)cyclohexyl]-N-methylbenzeneacetamide,
h.  4-azido-N-[4,4-diethoxy-2-(dimethylamino)cyclopentyl]-N-methylbenzamide,
i.  4-cyano-N-[4,4-dimethoxy-2-(diethylamino)cyclohexyl]-N-methylbenzeneacetamide,
j.  4-methanesulfonyl-N-[4,4-dimethoxy-2-(1-piperidinyl)-cyclohexyl]-N-methylbenzamide,
k.  4-methoxycarbonyl-N-[5,5-diethoxy-2-(dimethylamino)cycloheptyl]-N-methylbenzeneacetamide,
l.  4-acetyloxy-N-[4,4-dimethoxy-2-(1-pyrrolidinyl)cyclohexyl]-N-methylbenzeneacetamide,
m.  4-acetylamino-N-[4,4-diethoxy-2-(1-azetidinyl)cyclohexyl]-N-ethylbenzeneacetamide,
n.  4-methoxy-3-chloro-N-[4,4-dimethoxy-2-(diallylamino)cyclohexyl]-N-methylbenzeneacetamide,
o.  4-phenyl-N-[4,4-diethoxy-2-aminocyclohexyl]-N-methylbenzamide,
p.  3,4-dichloro-N-[4,4-dimethoxy-2-(1-pyrrolidinyl)cyclohexyl]-benzeneacetamide,
q.  4-bromo-N-[5,5-diethoxy-2-(1-azetidinyl)cycloheptyl]benzamide,
r.  N-[4,4-bis(methylthio)-2-(1-pyrrolidinyl)cyclopentyl]-3,4-dichloro-N-methylbenzeneacetamide,
s.  N-[4,4-bis(methylthio)-2-(1-pyrrolidinyl)cyclopentyl]-4-bromo-N-methylbenzamide,
t.  N-[4,4-bis(methylthio)-2-(1-pyrrolidinyl)cyclohexyl]-3,4-dichloro-N-methylbenzeneacetamide,
u.  N-[4,4-bis(methylthio)-2-(1-pyrrolidinyl)cyclohexyl]-4-bromo-N-methylbenzamide, v. N-[5,5-bis(ethylthio)-2-(1-pyrrolidinyl)cyclohexyl]-3,4-dichloro-N-methylbenzeneacetamide,
w. N-[4,4-bis(methylthio)-2-(1-pyrrolidinyl)cyclohexyl]-3,4-dichloro-N-methylbenzeneethanethioamide,
x. N-[4,4-bis(methylthio)-2-(1-pyrrolidinyl)cycloheptyl]-3,4-dichloro-N-methylbenzeneacetamide,
y. N-[5,5-bis(ethylthio)-2-(1-pyrrolidinyl)cycloheptyl]-4-bromo-N-methylbenzamide,
z. N-[6,6-bis(methylthio)-2-(1-pyrrolidinyl)cycloheptyl]-3,4-dichloro-N-methylbenzeneacetamide,
aa. 3,4-dichloro-N-[4,4-dimethoxy-2-(1-pyrrolidinyl)cyclohexyl]-N-methylbenzeneethanethioamide,
bb. 4-bromo-N-[4,4-dimethoxy-2-(1-pyrrolidinyl)cyclohexyl]-N-methylbenzenecarbothioamide,
cc. 3,4-dichloro-N-[5,5-dimethoxy-2-(1-pyrrolidinyl)cyclohexyl]-N-methylbenzeneethanethioamide,
dd. 4-bromo-N-[5,5-diethoxy-2-(1-pyrrolidinyl)cyclohexyl]-N-methylbenzenecarbothioamide,
ee. 3,4-dichloro-N-[6,6-dimethoxy-2-(1-pyrrolidinyl)cycloheptyl]-N-ethylbenzeneethanethioamide,
ff. 4-bromo-N-[4,4-diethoxy-2-(1-pyrrolidinyl)cycloheptyl]-N-(1-propyl)benzenecarbothioamide,
gg. 3,4-dichloro-N-[4,4-dimethoxy-2-(1-pyrrolidinyl)cyclopentyl]-N-methylbenzeneethanethioamide,
hh. 4-bromo-N-[4,4-dimethoxy-2-(1-pyrrolidinyl)cyclopentyl]-N-methylbenzenecarbothioamide,
ii. 3,4-dichloro-N-[4-methylthio-2-(1-pyrrolidinyl)cyclopentyl]-N-methylbenzeneacetamide,
jj. 4-bromo-N-[4-methylthio-2-(1-pyrrolidinyl)cyclopentyl]-N-methylbenzamide,
kk. 3,4-dichloro-N-[4-methylthio-2-(1-pyrrolidinyl)cyclohexyl]-N-methylbenzeneacetamide,
ll. 4-bromo-N-[4-methylthio-2-(1-pyrrolidinyl)cyclohexyl]-N-methylbenzamide,
mm. 3,4-dichloro-N-[5-ethylthio-2-(1-pyrrolidinyl)cyclohexyl]-N-methylbenzeneacetamide,
nn. 4-bromo-N-[5-(1-propylthio)-2-(1-pyrrolidinyl)cyclohexyl]-N-methylbenzamide,
oo. 3,4-dichloro-N-[6-methylthio-2-(1-pyrrolidinyl)cycloheptyl]-N-methylbenzeneacetamide,
pp. 4-bromo-N-[4-methylthio-2-(1-pyrrolidinyl)cycloheptyl]-N-methylbenzamide,
qq. 3-chloro-N-[5,5-dimethoxy-2-(1-piperidinyl)cyclohexyl]-N-ethylbenzeneethanethioamide,
rr. N-[4,4-diethoxy-2-(1-azetidinyl)cycloheptyl]-4-methylbenzeneethanethioamide,
ss. N-[6,6-diethoxy-2-[1-(dimethylamino)cycloheptyl]]-N-(1-propyl)-4-(trifluoromethyl)benzenecarbothioamide,
tt. N-[5,5-bis(methylthio)-2-[1-(diethylamino)cycloheptyl]]-N-methylbenzeneethanethioamide,
uu. N-[4-(ethylthio)-2-(diallylamino)cyclopentyl]-N-ethyl-4-nitrobenzamide,
vv. 4-methoxy-N-methyl-N-[4-(methylthio)-2-(1-pyrrolidinyl)cyclopentyl]benzeneacetamide,
ww. 4-hydroxy-N-methyl-N-[5-(1-propylthio)-2-aminocycloheptyl]benzeneacetamide,
xx. 3-azido-N-[4,4-bis(ethylthio)-2-aminocyclohexyl]-N-(1-propyl)benzamide,
yy. N-[5,5-bis(methylthio)-2-(1-azetidinyl)cyclohexyl]-N-methyl-[1,1'-biphenyl]-4-ethanethioamide,
zz. N-[4,4-bis(ethylthio)-2-(1-piperidinyl)cyclopentyl]-4-(methanesulfonyl)-N-(1-methylethyl)benzamide,
aaa. N-[4,4-bis(ethylthio)-2-(ethylmethylamino)cycloheptyl]-2-cyano-N-ethylbenzeneacetamide,
bbb. 4-amino-N-[6,6-bis(methylthio)-2-(methylpropylamino)cycloheptyl]-N-methylbenzenecarbothioamide,
ccc. 3,4-dichloro-N-[4-mercapto-2-(1-pyrrolidinyl)cyclopentyl]-N-methylbenzeneacetamide,
ddd. 4-bromo-N-[4-mercapto-2-(1-pyrrolidinyl)cyclopentyl]-N-methylbenzamide,
eee. 3,4-dichloro-N-[4-mercapto-2-(1-pyrrolidinyl)cyclohexyl]-N-methylbenzeneacetamide,
fff. 4-bromo-N-[4-mercapto-2-(1-pyrrolidinyl)cyclohexyl]-N-methylbenzamide,
ggg. 3,4-dichloro-N-[5-mercapto-2-(1-pyrrolidinyl)cyclohexyl]-N-methylbenzeneacetamide,
hhh. 4-bromo-N-[5-mercapto-2-(1-pyrrolidinyl)cyclohexyl]-N-methylbenzamide,
iii. 3,4-dichloro-N-[5-mercapto-2-(1-pyrrolidinyl)cycloheptyl]-N-methylbenzeneacetamide,
jjj. 4-bromo-N-[4-mercapto-2-(1-pyrrolidinyl)cycloheptyl]-N-methylbenzamide,
kkk. 3,4-dichloro-N-[5-mercapto-2-(1-pyrrolidinyl)cycloheptyl]-N-methylbenzeneethanethioamide, and the like.

CHART A

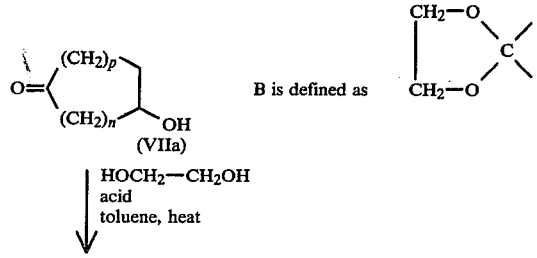

-continued
CHART A
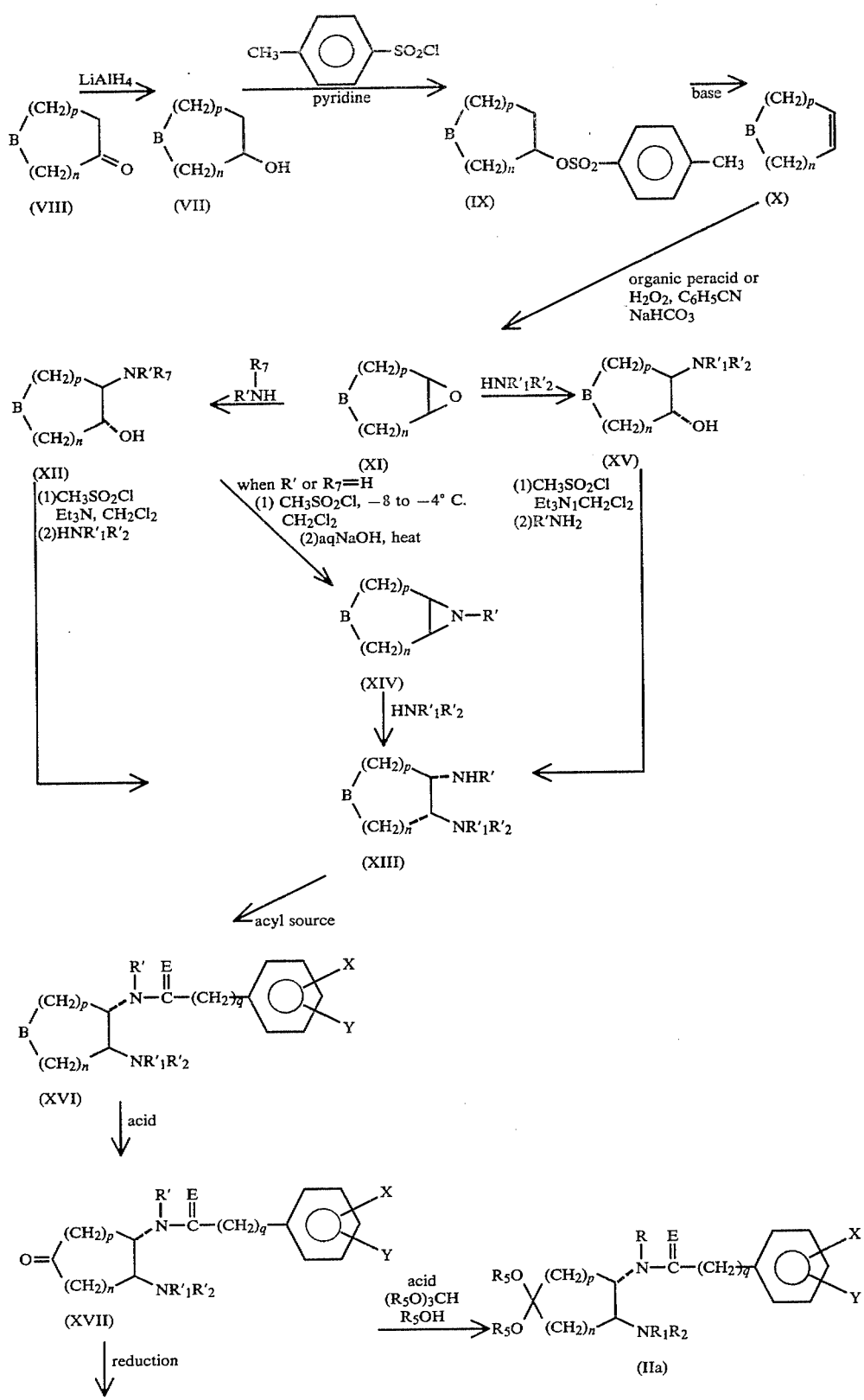

-continued
CHART A
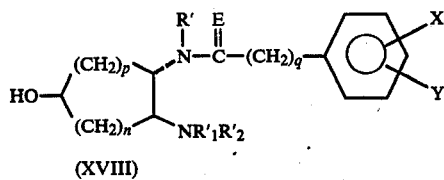
(XVIII)
CHART B
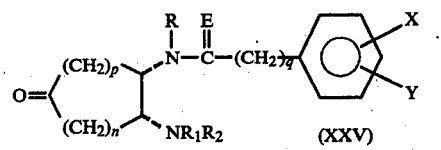
(XXV)
↓ (R5O)3CH
R5OH
acid
-continued
CHART B
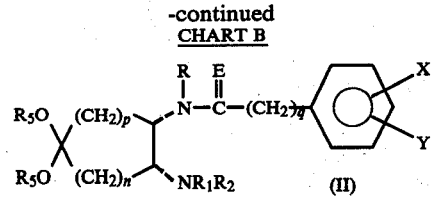
(II)
CHART C
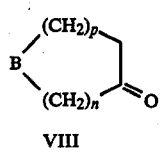
VIII
↓ HNR'1R'2
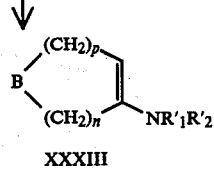
XXXIII
↓
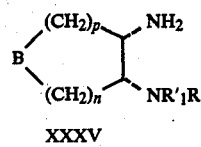
XXXV
↓ alkylation-(if desired)
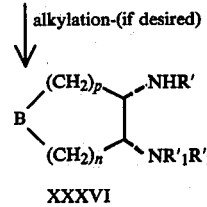
XXXVI
NaH
ClCO2R8 →
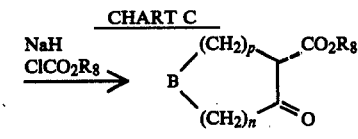
XXXI
↓ HNR'1R'2
ClCO2R8 →
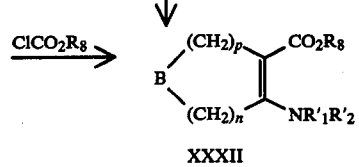
XXXII
↓ H2, PtO2
1. base
2. Curtius
reaction
←
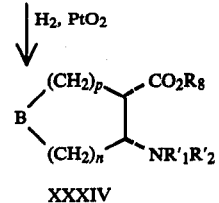
XXXIV
acyl source →
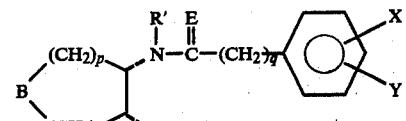
XXXVII
↓
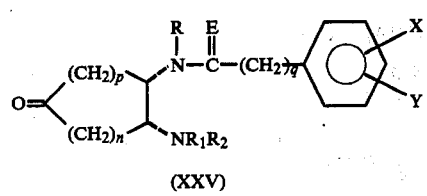
(XXV)

CHART D

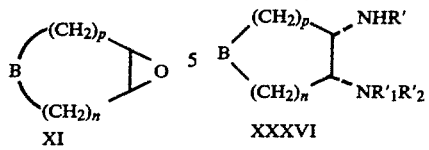
XI

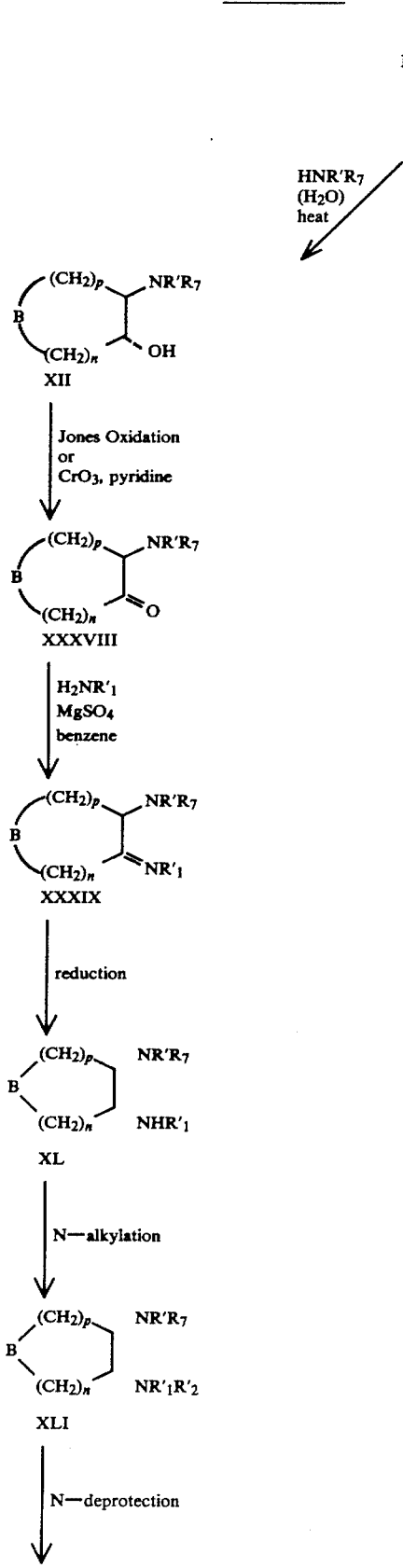

-continued
CHART D

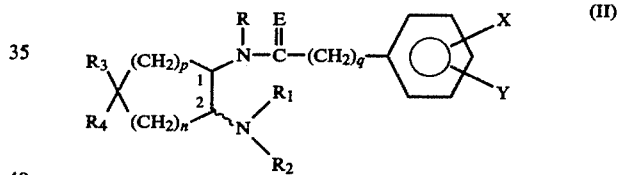

We claim:
1. A compound of the formula

$$R_3 \underset{R_4}{\overset{(CH_2)_p}{\diagdown}} \underset{(CH_2)_n}{\overset{1}{\underset{2}{\diagdown}}} \overset{R}{\underset{N}{\mid}} \overset{E}{\underset{\parallel}{-}} \overset{}{\underset{}{C}} -(CH_2)_q - \bigcirc \overset{X}{\underset{Y}{}} \quad (II)$$

with $R_1$, $R_2$ on the ring nitrogen wherein
p and n are each full number integers of from 1 to 3, so that the resulting cycloaliphatic ring has five to seven carbon atoms; the wavy line bond (~) between the nitrogen in the 2-position and the cycloaliphatic ring carbon indicates the bond can be either cis- or trans- with respect to each substituent on the cycloaliphatic ring;
q is 0 or 1;
X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino [(—NHC(O)R$_6$];
R is hydrogen or $C_1$ to $C_3$-alkyl;
$R_1$ and $R_2$, taken separately, are hydrogen, $C_1$ to $C_3$-alkyl, allyl; or
$R_1$ and $R_2$, taken together with the nitrogen to which they are bonded, complete a ring selected from the group consisting of azetidinyl, pyrrolidinyl, and piperidinyl;
$R_3$, taken separately, is hydrogen, and
$R_4$, taken separately, is mercapto(SH), —S—($C_1$-$C_3$-alkyl), or
$R_3$ is —GR$_5$ and $R_4$ is —GR$_5$;

wherein E is bivalent sulfur or oxygen;
each G is bivalent sulfur or oxygen;
$R_5$ is $C_1$ to $C_2$-alkyl;
$R_6$ is H or $C_1$ to $C_2$-alkyl;
or a pharmacologically acceptable acid addition salt thereof.

2. A compound according to claim 1 wherein p is 1 to 3, n is 1 to 3, and p and n are selected so that the cycloaliphatic ring has 5 to 7 ring carbon atoms, q is 0 or 1;
  at least one of X and Y is a halogen having an atomic number of from 9 to 35 in the 3- or 4-position of the phenyl ring, or both of X and Y are such a halogen in the 3- and 4-positions of the phenyl ring;
  R is $C_1$ to $C_3$-alkyl;
  $R_1$ and $R_2$ are taken together with the nitrogen to which they are bonded to complete an azetidinyl, pyrrolidinyl, or piperidinyl group;
  E is oxygen;
  $R_3$ and $R_4$ are each —$GR_5$, where each G is oxygen and $R_5$ is $C_1$ to $C_2$-alkyl,
  or a pharmacologically acceptable salt thereof.

3. A compound according to claim 2 which is 3,4-dichloro-N-[4,4-dimethoxy-2-(1-pyrrolidinyl)cyclohexyl]-N-methylbenzeneacetamide, or a pharmacologically acceptable salt thereof.

4. A compound according to claim 3 which is (±)-(1α, 2β)-3,4-dichloro-N-[4,4-dimethoxy-2-(1-pyrrolidinyl)cyclohexyl]-N-methylbenzeneacetamide, or a pharmaceutically acceptable salt thereof.

5. A composition useful in pharmaceutically effective dosage unit form for alleviating pain in warm-blooded mammals which comprises a compound of Formula II in claim 1 in combination with a pharmaceutically acceptable carrier.

6. A method of alleviating pain in a warm-blooded animal which comprises administering to an animal suffering pain an effective amount of a compound of claim 1 in a pharmaceutically acceptable dosage unit form.

7. A composition of claim 5 wherein the compound of Formula II is:

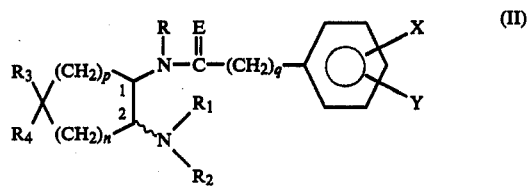

wherein
  p is 1 to 3, n is 1 to 3, and p and n are selected so that the cycloaliphatic ring has 5 to 7 ring carbon atoms, q is 0 or 1;
  at least one of X and Y is a halogen having an atomic number from 9 to 35 in the 3- or 4-position of the phenyl ring, or both of X and Y are such a halogen in the 3- and 4-positions of the phenyl ring;
  R is $C_1$ to $C_3$-alkyl;
  $R_1$ and $R_2$ are taken together with the nitrogen to which they are bonded to complete an azetidinyl, pyrrolidinyl, or piperidinyl group;
  E is oxygen;
  $R_3$ and $R_4$ are each —$GR_5$, where each G is oxygen and $R_5$ is $C_1$ to $C_2$-alkyl,
  or a pharmacologically acceptable salt thereof.

8. A composition of claim 5 wherein the compound is 3,4-dichloro-N-[4,4-dimethoxy-2-(1-pyrrolidinyl)cyclohexyl]-N-methylbenzeneacetamide, or a pharmacologically acceptable salt thereof.

* * * * *